United States Patent [19]

Labrie

[11] Patent Number: 5,023,234

[45] Date of Patent: Jun. 11, 1991

[54] COMBINATION MALE BREAST CANCER THERAPY

[76] Inventor: Fernand Labrie, 2735 boul Liegeois, St-Foy, Quebec, Canada, G1W 1Z9

[21] Appl. No.: 699,710

[22] Filed: Feb. 8, 1985

[51] Int. Cl.$^5$ .................... A61K 37/02; C07K 7/06
[52] U.S. Cl. .................... 514/15; 514/392; 514/649
[58] Field of Search .................... 514/15

[56] References Cited

PUBLICATIONS

Chem. Abstr., vol. 102, (1985) 198133.
Chem. Abstr., vol. 101, (1984) 33528.
Chem. Abstr., vol. 85, (1976) 57322.
Chem. Abstr., vol. 100, (1984) 203971.
Chem. Abstr., vol. 96, (1982) 1121.
Chem. Abstr., vol. 102, (1985) 106663.
Chem. Abstr., vol. 100, (1984) 151639
Chem. Abstr., vol. 100, 185795 (1984).
Chem. Abstr., vol. 95, (1981) 773.
Chem. Abstr., vol. 100, (1984) 17879.
Chem. Abstr., vol. 98, (1983) 173536.
Chem. Abstr., vol. 86, (1977) 84114.
Santen, R. et al., "Decreased LH BIO/Immuno Ratio During Treatment with the Superagonist Analog of GnRH, Leuprolide, for Prostate Carcinoma" in Abstracts of the 7th International Congress of Endocrinology, Jul. 1-7, 1984, Ab #2254, p. 138.
R. J. Donnelly, "Continuous Subcutaneous Administration of 'Zoladex' (ICI 118,630 an LH-RH Analogue) to Patients with Advanced Prostatic Cancer" in the Journal of Steroid Biochemistry, vol. 20 (#6B), Jun. 1984, p. 1375.

*Primary Examiner*—Lester L. Lee
*Attorney, Agent, or Firm*—Ostrolenk, Faber, Gerb & Soffen

[57] ABSTRACT

A method of treatment of breast cancer in susceptible male animals whose testicular hormonal secretions are blocked by surgical or chemical means, e.g., by use of an LH-RH agonist, e.g., [D-Trp$^6$, des-Gly-NH$_2^{10}$]LH-RH ethylamide which comprises administering an antiandrogen, e.g., flutamide and optionally at least one inhibitor of sex steroid biosynthesis, e.g., aminoglutethimide and/or ketoconazole. Pharmaceutical compositions useful for such treatment are also disclosed.

35 Claims, 3 Drawing Sheets

COMBINATION MALE BREAST CANCER THERAPY

BACKGROUND OF THE INVENTION

This invention relates to a method of treatment of breast cancer in susceptible warm-blooded male animals including humans using a therapy comprising administering an antiandrogen to such animals after the hormone output of their testes has been blocked by surgical or chemical means. The invention also includes pharmaceutical compositions useful for such treatment. In its most preferred aspect, this invention relates to treatment of hormone-dependent breast cancer in warm-blooded male animals by parenterally administering an LH-RH agonist or antagonist in association with orally administering an antiandrogen.

While various investigators have been studying hormone-dependent breast and prostate cancer, none have proposed the combination therapy of this invention.

A. V. Schally et al., Cancer Treatment Reports, 68, (No. 1) 281-289 (1984), summarize the results of animal and clinical studies on growth inhibition of hormone-dependent mammary and prostate tumors by use of analogues of luteinizing hormone-releasing hormones, the so-called LH-RH agonists and suggest that LH-RH analogs and/or antagonists may have potential for treating breast cancer.

T. W. Redding and A. V. Schally, Pro. Natl. Acad. Sci. USA, 80, 1459-1462 (1983), disclose reduction of estrogen-dependent mammary tumors in rats and mice by use of an LH-RH agonist, [D-Trp$^6$]LH-RH or of two specific antagonists.

In U.S. Pat. No. 4,071,622, it is disclosed that use of certain LH-RH agonists causes regression of DMBA-induced mammary carcinoma in rats.

In U.S. Pat. No. 4,472,382, it disclosed that prostate adenocarcinoma, benign prostate hypertrophy and hormone-dependent mammary tumors may be treated with various LH-RH agonists and that prostate adenocarcinoma and benign hypertrophy may be treated by use of various LH-RH agonists and an antiandrogen. However, there is no suggestion or disclosure of the present invention.

Some clinical improvement in premenopausal women with breast cancer by use of the two LH-RH agonists, Buserelin and Leuprolide, is also reported by H. A. Harvey et al. "LH-RH analogs in the treatment of human breast cancer", *LH-RH and its Analogs-A New Class of Contraceptive and Therapeutic Agents* (B. H. Vickery and J. J. Nestor, Jr., and E. S. E. Hafez, eds) Lancester, MTP Press, (1984) and by J. G. M. Klijn et al. "Treatment with luteinizing hormone releasing hormone analogue (Buserelin) in premenopausal patients with metastatic breast cancer", Lancet, 1, 1213-1216 (1982).

Treatment of advanced breast cancer with aminoglutethimide after therapy with the antiestrogen, Tamoxifen is disclosed by A. V. Buzdar et al., Cancer, 50, 1708-1712 (1982).

H. Flax et al., Lancet, 1204-1207, (1973), suggest some women's breast cancers are androgen-dependent.

F. Labrie et al., The Prostate, 4, 579-594 (1983), disclose that use of a combination therapy of an LH-RH agonist (Buserelin) and an antiandrogen (Anandron) to treat advanced prostate cancer in previously untreated patients effects simultaneous elimination of androgens of both testicular and adrenal origin.

F. Labrie et al., J. Steroid Biochem., 19, 9-1007 (1983), disclose the treatment of prostate cancer by the combined administration of an LH-RH agonist and an antiandrogen. Labrie et al. disclose animal and clinical data in support of the proposition that the combined LH-RH/antiandrogen treatment neutralizes the stimulatory influence of all androgens on the development and growth of androgen-dependent prostatic cancer.

In U.S. Pat. No. 4,094,994, it is disclosed that the use of antiestrogens such as meso-3,4-bis(3'-hydroxyphenyl)hexane inhibits MCF7 human breast tumor cells. In fact, the inhibitory activity of the anti-estrogen was antagonized by estradiol.

H. Mouridsen et al,. Cancer Treatment Review 5, 131-141, (1978), disclose that Tamoxifen, an antiestrogen is effective in remission of advanced breast cancer in about 30% of the patients treated.

J. G. M. Klijn et al., (J. Steroid Biochem, Vol. 20 (No. 6B), 1381 (1984), disclosed the combined use of the antiestrogen, Tamoxifen, and the LH-RH agonist, Buserelin, for treatment of breast cancer is known, but objective remission of such cancers remains low (35%).

BRIEF DESCRIPTION OF THE INVENTION

In one aspect, the invention provides a method of treating breast cancer in a warm-blooded male animal in need of such treatment which comprises blocking the testicular hormonal secretions of said animal by surgical or chemical means and administering to said animal a therapeutically effective amount of an antiandrogen, or a pharmaceutical composition thereof. In another aspect, the invention provides a method of treating breast cancer in a castrated warm-blooded male animal, i.e., such a male animal whose testes were previously blocked by surgical or chemical means from secreting androgen, which comprises administering to an animal in need of such treatment therapeutically effective amounts of an antiandrogen in association with at least one inhibitor of sex steroid biosynthesis, or a pharmaceutical composition thereof, in an amount sufficient to treat breast cancer. By simultaneously blocking sex-steroids (androgens and estrogens of testicular and adrenal origin) production and/or action, the present invention provides a method of inhibiting the growth of hormone-sensitive breast tumors in warm-blooded male animals having such tumors.

In male mammals, the removal of testicular androgens may be achieved by surgical castration but preferably the secretion of androgens from the testes is blocked by chemical castration by administering to warm-blooded male animal, an effective amount of an LH-RH agonist or antagonist. Thus, in a preferred aspect, the present invention provides a method of treating breast cancer in a warm-blooded male animal, which comprises administering to an animal in need of such treatment an LH-RH agonist or antagonist in association with an antiandrogen, or a pharmaceutical composition thereof, in amounts sufficient to treat breast cancer.

In its preferred aspect, the LH-RH agonist is administered parenterally (subcutaneously or intramuscularly) and the antiandrogen is administered orally.

DETAILED DESCRIPTION OF THE INVENTION

In one preferred aspect, the present invention provides an effective method of treating breast cancer in warm-blooded male animals in need of such treatment by administering a LH-RH agonist or antagonist in association with an antiandrogen or pharmaceutical compositions thereof in amounts sufficient to inhibit breast tumor growth. In another preferred aspect, the use of an LH-RH agonist in association with an antiandrogen produced almost complete blockage of testicular steroid secretion while simultaneously blocking about 25 to 60% of the precursor sex steroids (androgens and estrogens) of adrenal origin. See FIG. 3 and the Example. In still another preferred aspect, at least one inhibitor of sex steroid biosynthesis is administered to warm-blooded male animals having breast cancer in association with surgical castration or chemical castration (by use of an LH-RH agonist or antagonist) and the antiandrogen for treatment of breast cancer. These active compounds can be administered together or in any order as discussed hereinafter. To assist in determining the effect of the treatment, blood plasma concentrations of the adrenal androgens and estrogens and tumor size are measured. Lowered concentrations of sex steroids and reduction in tumor size are indicative of successful treatment, e.g. inhibition of tumor growth. The concentrations of adrenal androgens and estrogens such as dehydroepiandrosterone (DHEA), DHEA-sulfate (DHEAS), androst-5-ene-3b, 17b-diol ($W^5$-diol) and, the estrogen, 17b-estradiol ($E_2$) are measured by standard methods well known to those skilled in the art, see for example F. Labrie et al., The Prostate, 4, 579–594 (1983).

Figure 1:
FIG. 1 is a bone scintigraph showing multiple bone metastases in a patient having breast cancer prior to treatment in accordance with an aspect of the present invention.

The active compounds described herein and used in accordance with the present invention exhibited tumor growth inhibition and lowered concentrations of sex steroids when tested in warm-blooded male animals including man. See FIG. 1-2 and 3 and the descriptions thereof in the Example.

The change in tumor size is measured by standard physical methods well known to those skilled in the art, e.g., bone scan, chest X-ray, skeletal survey, ultrasonography of the liver and liver scan (if needed), CAT-scan and physical examination.

While a LH-RH agonist or a LH-RH antagonist may be used in one preferred aspect of the present invention, the use of a LH-RH agonist is more preferred.

By the term "LH-RH agonist" is meant synthetic analogues of the natural luteinizing hormone-releasing hormone (LH-RH), a decapeptide of the structure:

L—pyroglutamyl—L—histidyl—L—tryptophyl—

L—seryl—L—tyrosyl—glycyl—L—leucyl—

L—arginyl—L—prolylglycyl—$NH_2$

Typical suitable LH-RH agonists include nonapeptides and decapeptides represented by the formula:

L—pyroglutamyl—L—histidyl—L—tryptophyl—L—seryl—

—L—tyrosyl—X—Y—L—arginyl—L—prolyl—Z wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and Y is L-leucyl, D-leucyl, $N^\alpha$-methyl D-leucyl, $N^\alpha$-methyl-L-leucyl or D-alanyl and wherein Z is glycyl-$NHR_1$ or $NHR_1$ wherein $R_1$ is H, lower alkyl or lower haloalkyl. Lower alkyl includes straight or branched chain alkyls having 1 to 6 carbon atoms, e.g., methyl, ethyl, propyl, pentyl or hexyls, iso-butyl, neopentyl and the like. Lower haloalkyl includes straight and branched chain alkyls of 1 to 6 carbon atoms having a halogen substituent, e.g., —$CF_3$, —$CH_2CF_3$, —$CF_2CH_3$. Halogen means F, Cl, Br, with F being preferred.

Preferred nonapeptides wherein Y is L-leucyl and X is an optically active D-form of selected amino acids and Z is $NHC_2H_5$ are [D-Trp$^6$, des-gly-$NH_2^{10}$]-LH-RH ethylamide (X=D-Trp$^6$); [D-Ser-(t-BuO)$^6$, des-gly-$NH_2^{10}$]-LH-RH ethylamide [X=D-Ser(t-BuO)$^6$]; [D-Leu$^6$, des-gly-$NH_2^{10}$]-LH-RH ethylamide (X=D-Leu$^6$), [D-His(Bzl)$^6$, des-gly-$NH_2^{10}$]LH-RH ethylamide (X=iminobenzyl-D-His$^6$) and [D-Ala$^6$, des-gly-$NH_2^{10}$]-LH-RH ethylamide (X=D-Ala$^6$).

Preferred decapeptides include [D-Trp$^6$]-LH-RH wherein X=D-Trp, Y=L-leucyl, Z=glycyl-$NH_2$, [D-Phe$^6$]-LH-RH wherein X=D-phenylalanyl, Y=L-leucyl and Z=glycyl-$HN_2$) or [D-Nal(2)$^6$]LH-RH which is [(3-(2-naphthyl)-D-Ala$^6$]LH-RH wherein X=3-(2-naphthyl)-D-alanyl, Y=L-leucyl and Z=glycyl-$NH_2$.

Other LH-RH agonists useful within the scope of this invention are the α-aza analogues of the natural LH-RH, especially, [D-Phe$^6$, Azgly$^{10}$]-LH-RH, [D-Tyr(-Me)$^6$, Azgly$^{10}$]-LH-RH, and [D-Ser-(t-BuO)$^6$, Azgly$^{10}$]-LH-RH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LH-RH antagonists include [N-Ac-D-p-Cl-Phe$^{1,2}$, D-Phe$^3$, D-Arg$^6$, D-Ala$^{10}$]-LH-RH disclosed by J. Ercheggi et al., Biochem. Biophys. Res. Commun. 100, 915–920, (1981); [N-Ac-D-p-Cl-Phe$^{1,2}$, D-Trp$^3$, D-Arg$^6$, D-Ala$^{10}$]LH-RH disclosed by D. H. Coy et al., Endocrinology, 110: 1445–1447, (1982); [N-Ac-D-(3-(2-naphthyl)-Ala)$^1$, D-p-Cl-Phe$^2$, D-Trp$^3$, D-hArg(Et$_2$)$^6$,D-Ala$^{10}$]-LH-RH and [N-Ac-Pro$^1$, D-p-F-Phe$^2$, D-(3-(2-naphthyl)Ala$^{3,6}$]-LH-RH disclosed by J. J. Nestor et al. J. Steroid Biochem., 20 (No. 6B), 1366 (1984); the nona - and decapeptides analogs of LH-RH useful as LH-RH antagonists disclosed in U.S. Pat. No. 4,481,190 (J. J. Nestor et al.); analogs of the highly constrained cyclic antagonist, cycle [Δ$^3$ Pro$^1$, D-p-Cl-Phe$^2$, D-Trp$^{3,6}$, N-Me-Leu$^7$, β-Ala$^{10}$]-LH-RH disclosed by J. Rivier, J. Steroid Biochem., 20, (No. 6B), 1365 (1984), and [N-Ac-D-(3-(2-naphthyl)-Ala$^1$, D-p-F-Phe$^2$, D-Trp$^3$, D-Arg$^6$]-LH-RH disclosed by A. Corbin et al., J. Steroid Biochem. 20 (No. 6B) 1369 (1984).

Other LH-RH agonist and antagonist analogs are disclosed in LH-RH and Its Analogs, B. H. Vickory et al. editors at pages 3–10 (J. J. Nestor), 11–22 (J. Rivier et al.) and 23–33 (J. J. Nestor et al.)

The LH-RH agonists and antagonists useful in this invention may conveniently be prepared by the method described by Stewart et al. in "Solid Phase Peptide Synthesis" (published in 1969 by Freeman & Co., San Francisco, page 1) but solution phase synthesis may also be used.

The nona- and decapeptides used in this invention are conveniently assembled on a solid resin support, such as 1% cross-linked Pro-Merrifield resin by use of an automatic peptide synthesizer. Typically, side-chain protecting groups, well known to those in the peptide arts, are used during the dicyclohexylcarbodiimide-cataylzed coupling of a tert-butyloxycarbonylamino acid to the growing peptide attached to a benzhydrylamine resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration and partition chromatography and optionally lyophilization. See also D. H. Coy et al., J. Med. Chem. 19, pages 423–425. (1976).

Typical suitable antiandrogens include non-steroidal antiandrogens such as the imidazolidines, especially 1-(3'-trifluoromethyl-4'-nitrophenyl)-4,4-dimethyl-imidazoline-2,5-dione (also called Anandron) described in U.S. Pat. No. 4,097,578, or 4'-nitro-3'-trifluoromethylisobutyranilide (also called flutamide) described in U.S. Pat. No. 4,329,364 as well as the N-(phenylalkanoyl)aniline derivatives disclosed in U.S. Pat. No. 4,386,080 and the 3,4-disbustituted - branched-chain acylanilides disclosed in U.S. Pat. No. 4,239,776 (A. T. Glen et al). Flutamide is the preferred antiandrogen.

Typical suitable steroidal antiandrogens include 6-chloro-1,2-dihydro-17-(acetyloxy)-3'-H-cyclopropa[1,2]pregna-1,4,6-triene-3,20-dione, available under the tradename of Androcur from Schering A. G., W. Berlin.

The inhibitors of sex steroid biosynthesis found useful in the present invention include those compounds which inhibit biosynthesis of sex steroids and sex steroid precursors of testicular and/or adrenal origin, preferably of testicular and adrenal origin.

In another preferred aspect of the present invention, at least one inhibitor of sex steroid biosynthesis such as 3-(4-aminophenyl)-3-ethyl-2,6-piperidinedione, an adrenal sex steroid biosynthesis inhibitor which is commonly called aminoglutethimide and is available from Ciba Pharmaceutical Co., Summit N.J. under tradename Cytadren or ketoconazole, a testicular sex steroid biosynthesis inhibitor which is available from Janssen Pharmaceutical, Piscataway, N.J. under the tradename Nizoral is administered in combination with the LH-RH agonist or antagonist, and the antiandrogen for treatment of breast cancer.

When an inhibitor of adrenal sex steroid biosynthesis, e.g., aminoglutethimide is administered, cortisol biosynthesis is blocked. Accordingly, hydrocortisone is administered in physiological amounts sufficient to maintain normal glucocorticoid levels.

In this invention, the LH-RH agonist or antagonist and antiandrogen are administered as pharmaceutical compositions via topical, parenteral or oral means. The LH-RH agonist or antagonist is administered parenterally, i.e., intramuscularly, subcutaneously or intravenously by injection or infusion by nasal drops or by suppository. The LH-RH agonist or antagonist also may be microencapsulated in or attached to a biocompatable, biodegradable polymer, e.g., poly(d,1-lactide-co-glycolide) and subcutaneously or intramuscularly injected by a technique called subcutaneous or intramuscular depot to provide continuous, slow release of the LH-RH agonist or antagonist over a period of 30 days or longer. The most preferred route of administration of the LH-RH agonist or antagonist is subcutaneous depot injection. Preferably the antiandrogen will be administered orally. Preferably, the inhibitors of sex steroid biosynthesis such as aminoglutethimide and ketoconazole, when used, are administered orally.

The amount of each component administered is determined by the attending clinicians taking into consideration the etiology and severity of the disease, the patient's condition and age, the potency of each component and other factors.

The LH-RH agonist or antagonist is generally administered at from about 10 to 5000 $\mu$g per day, with contemplated dosage ranges of about 10 to 1500 $\mu$g per day and about 250 to 500 $\mu$g per day for the LH-RH agonist and to about 50 to 5000 $\mu$g per day for the LH-RH antagonist being preferred.

In the most preferred embodiment of this invention, the LH-RH agonist or antagonist is administered subcutaneously in a daily dose of 500 $\mu$g for the first 30 days and thereafter subcutaneously in a daily dose of 250 $\mu$g regardless of the patients' body weight. When the LH-RH agonist or antagonist is administered, once every 30-day period or even longer, by intramuscular or subcutaneous depot injection, a dose from about 300 to 150,000 $\mu$g per 30-day period is used, with a dose of 750 to 15,000 $\mu$g per 30-day period being preferred.

The antiandrogen compositions are generally administered in a dosage range of about 0.20 to 40 mg/kg (body weight) per day with 750 mg per day in three equally divided doses being preferred.

The aminoglutethimide compositions when used are administered initially in a dosage of 250 mg given at 8-hour intervals and the dosage may be increased in increments of 250 mg daily up to a total daily dose of 2 grams.

The ketoconazole compositions when used are administered orally in a dose of 250 mg given at 8-hour intervals and may be increased to a daily dose of 2 grams.

The LH-RH agonist or antagonist and anti-androgen and inhibitor of sex steroid biosynthesis each may be administered separately or when the modes of administration are the same, all or two of them may be administered in the same composition, but in any case the preferred ratio of LH-RH agonist to antiandrogen to inhibitor of sex steroid biosynthesis administered daily will be about 250 $\mu$g of LH-RH agonist to about 750 mg of antiandrogen to about 750 mg of inhibitor of sex steroid biosynthesis.

In the most preferred aspect of this invention, the LH-RH agonist is [D-Trp$^6$, des-Gly NH$_2^{10}$]LH-RH ethylamide which is administered subcutaneously in single daily dose of 500 $\mu$g for the first thirty (30) days of treatment and thereafter in a single daily dose of 250 $\mu$g; the antiandrogen is 4'-nitro-3'-trifluoromethylisobutyranilide, i.e., flutamide, which is administered orally in three equally divided daily doses of 250 mg; and the inhibitor of sex steroid biosynthesis is ketoconazole alone or in association with aminoglutethimide, each of which is administered orally in three equally divided doses of 250 mg every 8 hours.

The inhibitor(s) of sex steroid biosynthesis and the antiandrogen are preferably administered to a male in need of the breast cancer treatment of this invention one or two days before the LH-RH agonist or antagonist is administered, but the attending clinician may elect to start administration of the LH-RH agonist or antagonist, the antiandrogen and the inhibitor of steroid biosynthesis on the first day of the treatment.

When patients whose testes have already been surgically removed are treated according to this invention, the antiandrogen administration and dosage are the same as indicated when the antiandrogen is used in combination with the LH-RH agonist or antagonist as well as the third ingredient, i.e. the inhibitor of adernal steroid biosynthesis such as aminoglutethimide.

Normally, an inhibitor of testicular sex steroid biosynthesis such as ketoconazole may be administered to chemically but not surgically-castrated patients.

The LH-RH agonists or antagonists useful in the present invention are typically amorphous solids which are freely soluble in water or dilute acids, e.g., HCl, $H_2SO_4$, citric, acetic, mandelic or fumaric. The LH-RH agonist or antagonist for subcutaneous injection is supplied in vials containing 6 mL of sterile solution with the LH-RH agonist or antagonist at a concentration of about 1.0 mg/mL.

A typical pharmaceutical composition of the LH-RH agonists include the LH-RH agonist or a pharmaceutically acceptable acid salt thereof, benzyl alcohol, a phosphate buffer (pH=6.9-7.2) and sterile water.

The LH-RH agonist or antagonist for intramuscular or subcutaneous depot injection may be microencapsulated in a biocompatible, biodegradable polymer, e.g., poly (d,1-lactide-co-glycolide) by a phase separation process or formed into a pellet. The microspheres maybe then suspended in a carrier to provide an injectable preparation or the depot may be injected in the form of a pellet.

The aminoglutethimide and ketoconazole are typically compounded in customary ways for oral administration, e.g., in tablets, capsules and the like.

The antiandrogens useful in the present invention are typically formulated with conventional pharmaceutical excipients, e.g., spray dried lactose and magnesium stearate into tablets or capsules for oral administration. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste-improving substances can be added in the case of oral-administration forms.

As further forms of administration, one can use plug capsules, e.g., of hard gelatin, as well as closed soft-gelatin capsules comprising a softener or plasticizer, e.g., glycerine. The plug capsules contain the active substance preferably in the form of granulate, e.g., in mixture with fillers, such as lactose, saccharose, mannitol, starches, such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil.

Following the above treatment using the described regimen, breast tumor growth is inhibited and in some instances complete remission occurs.

The following example illustrates the invention.

EXAMPLE

Twelve months after modified radical mastectomy with axillary dissection (4 out of 13 positive nodes) in a 66-year old man, bone scintigraphy (FIG. 1) showed multiple bone metastatic lesions in the third and fourth cervical vertebrae, in the first, third and twelfth thoracic vertebrae, in the third, fourth and fifth lumbar vertebrae, in both sacro-iliac areas, in both shoulders and in the anterior part of the second right rib. Chest X-Ray and abdominal echogram did not show evidence of additional extension of the disease. The pituitary (LH, FSH and prolactin) as well as steroid [pregnenolone, 17-OH pregnenolone, dehydroepiandrosterone (DHEA), DHEA-sulfate, androst-5-ene-3$\beta$,17$\beta$-diol($\Delta^5$-diol), progesterone, 17-OH-progesterone, androstenedione($\Delta^4$-dione), testosterone (T), dihydrotestosterone (DHT), androstane-3$\alpha$,17$\beta$-diol, androstane-3$\beta$,17$\beta$-diol, androsterone and cortisol] hormones were within normal limits. Hormone measurements and calculations were performed as described hereinabove. The serum concentration of carcinoembryonic antigen (CEA) as well as a series of laboratory analyses, including complete blood count, sequential multiple analyzer (SMA-12) and urinalysis were normal.

Figure 2:
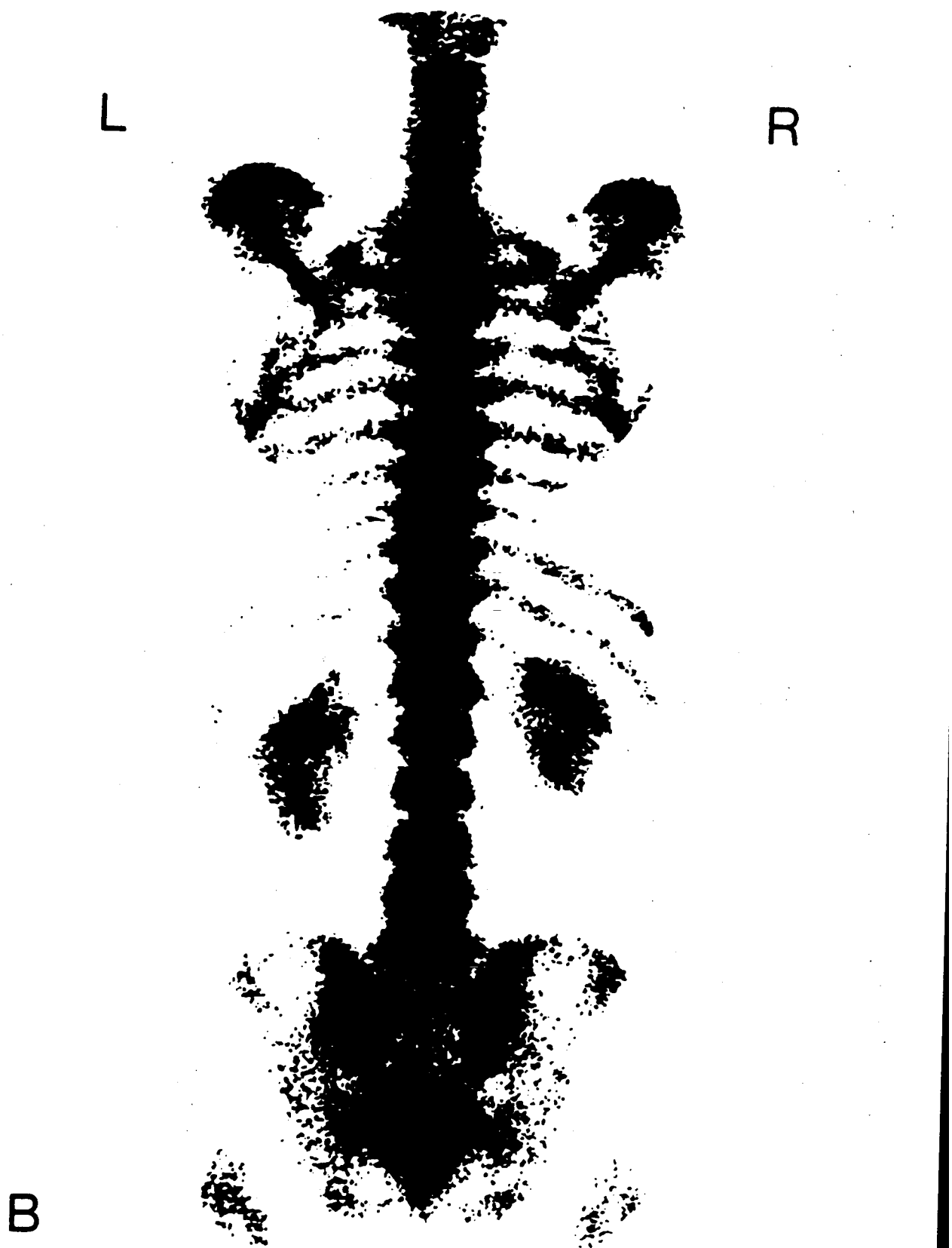
FIG. 2 is a bone scintigraph of the same patient after treatment for six and a half months in accordance with an aspect of the present invention.
Figure 3:
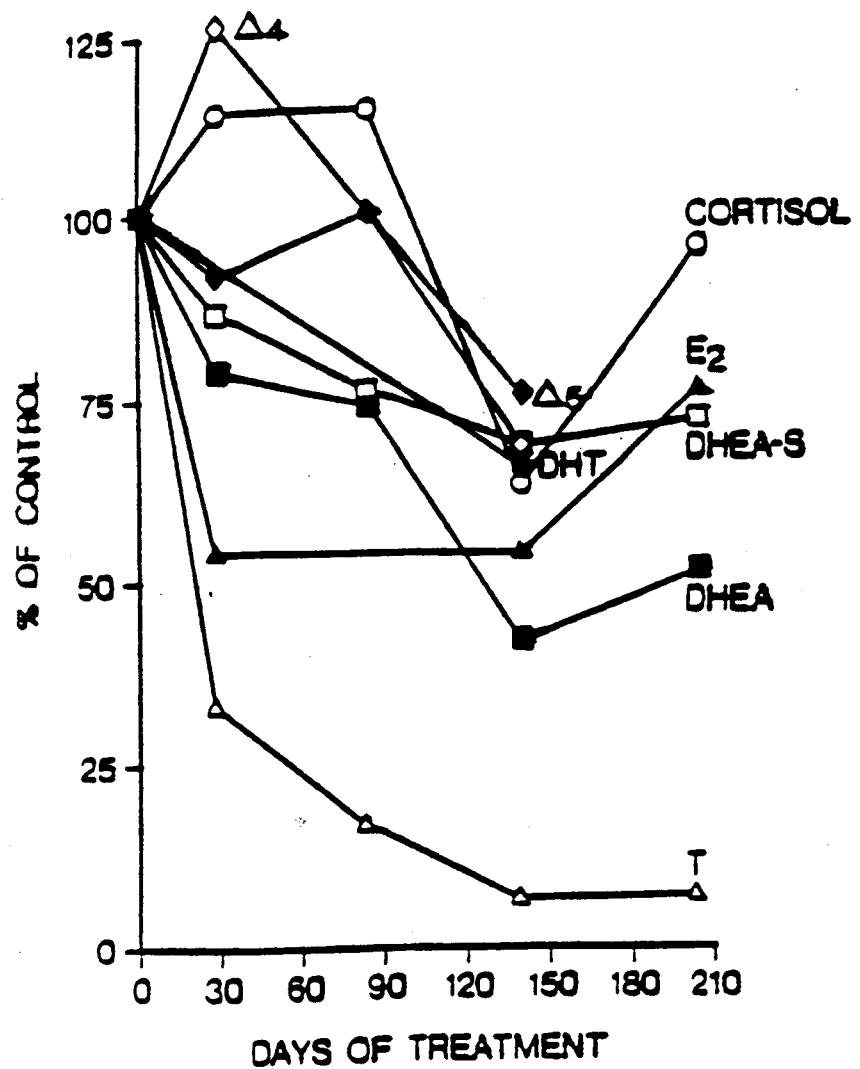
FIG. 3 graphically displays serum levels of testicular and adrenal steroids in a patient treated in accordance with an aspect of the present invention.

Combined antihormonal treatment with the LH-RH agonist [D-Ser-(tBuO)$^6$, des-gly-NH$_2^{10}$]LH-RH ethylamide (500 µg daily, s.c.) in combination with the pure antiandrogen Flutamide (250 mg orally every 8h) was started. Six and a half months later bone scintigraphy showed a complete disappearance of increased uptake in all the areas identified 6½ months earlier with no appearance of new lesion (FIG. 2). X-Ray, ultrasonography and clinical examination revealed no sign of any lesion. As illustrated in FIG. 3, the combined treatment caused 95% reduction (compared to control) in serum testosterone (T) and a 25 to 60% fall in the serum levels of adrenal steroids, namely DHEA, DHEAS, $\Delta^4$-dione and $\Delta^5$-diol while not affecting cortisol significantly. Serum levels of DHT and E$_2$ were also decreased by 20 to 40%. During hormonal therapy, no clinical sign of the disease could be detected. The only side-effects were related to hypoandrogenicity. Thus, after four months of treatment, the patient developed mild climateric-like vasomotor phenomena consisting of perspiration and hot flushes, which did not require treatment. He also complained of loss of libido and sexual potency after two months of treatment.

The present data show a rapid and complete regression of bone metastases in a patient having wide-spread bone metastases from breast cancer. A complete response could be seen within 6½ months after starting the combined treatment with an LH-RH agonist and a pure antiandrogen.

What is claimed:

1. A method of treating breast cancer in a warm-blooded male animal in need of such treatment which comprises blocking testicular hormonal secretions of said animal by surgical or chemical means and administering to said animal a therapeutically effective amount of an antiandrogen, or pharmaceutical compositions thereof.

2. The method of claim 1 wherein the testicular hormonal secretions are surgically blocked.

3. The method of claim 1 wherein the hormonal secretions are blocked by administering an amount of a LH-RH agonist or a LH-RH antagonist or a pharmaceutical composition thereof effective to block said hormonal secretions.

4. The method according to claim 1 wherein the LH-RH agonist is administered parenterally together with a pharmaceutically acceptable parenteral carrier.

5. The method of claim 1 wherein the anti-androgen is administered orally, together with a pharmaceutically acceptable oral carrier.

6. The method of claim 1 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and wherein Y is L-leucyl, D-leucyl, $N^\alpha$-methyl-D-leucyl, $N^\alpha$-methyl-L-leucyl or D-alanyl and wherein Z is glycyl-$NHR_1$ or $NHR_1$ wherein $R_1$ is H, lower alkyl or lower haloalkyl.

7. The method of claim 1 which further comprises administering an inhibitor of sex steroid biosynthesis or a pharmaceutical composition thereof.

8. The method of claim 7 wherein the inhibitor of sex steroid biosynthesis is aminoglutethimide and or ketoconazole.

9. The method of claim 1 wherein the anti-androgen is 1-(3'-trifluoromethyl-4'-nitrophenyl)-4,4-dimethylimidazoline-2,5-dione.

10. The method of claim 1 wherein the anti-androgen is 4'-nitro-3'-trifluoromethylisobutyranilide.

11. A method of treating breast cancer in a castrated warm-blooded male animal having breast cancer which comprises administering to said animal therapeutically effective amounts of an antiandrogen in association with at least one inhibitor of sex steroid biosynthesis or pharmaceutical compositions thereof.

12. The method of claim 11 wherein the testicular hormonal secretions have been surgically blocked and an inhibitor of adrenal sex steroid biosynthesis is administered in association with an antiandrogen or pharmaceutical compositions thereof.

13. The method of claim 11 wherein the hormonal secretions are blocked by administering an amount of a LH-RH agonist or a LH-RH antagonist or a pharmaceutical composition thereof effective to block said hormonal secretions.

14. The method of claim 11 wherein the association antiandrogen and said inhibitor(s) of sex steroid biosynthesis are each administered orally, together with a pharmaceutically acceptable oral carrier.

15. The method of claim 11 wherein one inhibitor of sex steroid biosynthesis or a pharmaceutical composition thereof is administered.

16. The method of claim 15 wherein the inhibitor of sex steroid biosynthesis is ketoconazole or a pharmaceutical composition thereof.

17. The method of claim 15 wherein the inhibitor of sex steroid biosynthesis is aminoglutethimide or a pharmaceutical composition thereof.

18. The method of claim 11 wherein two inhibitors of sex steroid biosynthesis or pharmaceutical compositions thereof are administered.

19. The method of claim 18 wherein the two inhibitors of sex steroid biosynthesis are aminoglutethimide and ketoconazole or pharmaceutical compositions thereof.

20. The method of claim 11 wherein the antiandrogen is 1-(3'-trifluoromethyl-4'nitrophenyl)-4,4-dimethylimidazoline-2,5-dione.

21. The method of claim 11 wherein the anti-androgen is 4'-nitro-3'-trifluoromethylisobutyranilide.

22. A method of treating breast cancer in a warm-blooded male animal having breast cancer which comprises administering to said animal therapeutically effective amounts of a LH-RH agonist or a LH-RH antagonist in association with an antiandrogen, or pharmaceutical compositions thereof.

23. The method of claim 22 wherein the LH-RH agonist or LH-RH antagonist is administered parenterally together with a pharmaceutically acceptable parenteral carrier.

24. The method of claim 22 wherein the antiandrogen is administered orally, together with pharmaceutically acceptable oral carrier.

25. The method of claim 22 wherein the LH-RH agonist is administered at a daily parenteral dose of between 10 and 1500 µg.

26. The method of claim 22 wherein the antiandrogen is administered at a daily oral dose of between about 0.20 and 40 mg/kg.

27. The method of claim 22 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and wherein Y is L-leucyl, D-leucyl, $N^\alpha$-methyl D-leucyl, $N^\alpha$-methyl-L-leucyl or D-alanyl and wherein Z is glycyl-$NHR_1$ or $NHR_1$ wherein $R_1$ is H, lower alkyl or lower haloalkyl.

28. The method of claim 22 which further comprises administering at least one inhibitor of sex steroid biosynthesis.

29. The method of claim 28 wherein one inhibitor of sex steroid biosynthesis or a pharmaceutical composition thereof is administered.

30. The method of claim 29 wherein the inhibitor of sex steroid biosynthesis is ketoconazole or a pharmaceutical composition thereof.

31. The method of claim 29 wherein the inhibitor of sex steroid biosynthesis is aminoglutethimide or a pharmaceutical composition thereof.

32. The method of claim 28 wherein two inhibitors of sex steroid biosynthesis or a pharmaceutical composition thereof are administered.

33. The method of claim 32 wherein the two inhibitors of sex steroid biosynthesis are aminoglutethimide and ketoconazole or pharmaceutical compositions thereof.

34. The method of claim 22 wherein the antiandrogen is 1-(3'-trifluoromethyl-4'-nitrophenyl)-4,4-dimethylimidazoline-2,5-dione.

35. The method of claim 22 wherein the anti-androgen is 4'-nitro-3'-trifluoromethylisobutyranilide.

* * * * *